US 12,418,536 B2

(12) United States Patent
Ainsworth et al.

(10) Patent No.: US 12,418,536 B2
(45) Date of Patent: Sep. 16, 2025

(54) METHODS AND SYSTEM FOR CONTROLLING ACCESS TO ENTERPRISE RESOURCES BASED ON TRACKING

(71) Applicant: Tyco Fire & Security GmbH, Neuhausen am Rheinfall (CH)

(72) Inventors: Peter Alexander Ainsworth, Oxfordshire (GB); Ian C. Westmacott, Tewksbury, MA (US); Martin J. Donaghy, Antrim (GB); Derek Boyes, Armagh (GB); Terry Neill, Antrim (GB); John McKenna, County Derry (GB); Anne Gallagher, Belfast (GB); Mark Paterson, Newtownards Down (GB); Ashish Italiya, Newtownabbey (GB)

(73) Assignee: Tyco Fire & Security GmbH, Neuhausen am Rheinfall (CH)

( * ) Notice: Subject to any disclaimer, the term of this patent is extended or adjusted under 35 U.S.C. 154(b) by 413 days.

(21) Appl. No.: 16/757,129

(22) PCT Filed: Nov. 2, 2018

(86) PCT No.: PCT/US2018/058971
§ 371 (c)(1),
(2) Date: Apr. 17, 2020

(87) PCT Pub. No.: WO2019/090087
PCT Pub. Date: May 9, 2019

(65) Prior Publication Data
US 2020/0344238 A1    Oct. 29, 2020

Related U.S. Application Data

(60) Provisional application No. 62/581,207, filed on Nov. 3, 2017.

(51) Int. Cl.
*H04L 9/40* (2022.01)
*A61B 5/1171* (2016.01)
(Continued)

(52) U.S. Cl.
CPC .......... *H04L 63/102* (2013.01); *A61B 5/1176* (2013.01); *A61B 5/165* (2013.01);
(Continued)

(58) Field of Classification Search
CPC ..... H04L 63/102; H04L 63/105; H04N 7/181; H04W 4/029; H04W 4/023; G07C 9/30;
(Continued)

(56) References Cited

U.S. PATENT DOCUMENTS 4,777,478 A    10/1988  Hirsch et al.
6,904,168 B1    6/2005  Steinberg et al.
(Continued)

FOREIGN PATENT DOCUMENTS

CN          105516659 A        4/2016
DE    10 2009 000 006          7/2010
(Continued)

OTHER PUBLICATIONS

International Search Report and Written Opinion of the International Searching Authority, mailed on Dec. 21, 2018, from International Application No. PCT/US2018/058971, filed on Nov. 2, 2018, 8 pages.
(Continued)

*Primary Examiner* — Gil H. Lee
(74) *Attorney, Agent, or Firm* — ArentFox Schiff LLP

(57) ABSTRACT

Methods and systems for controlling access to enterprise resources based on tracking are disclosed. In one implementation, an enterprise security system includes one or more tracking systems, an information technology (IT) system, and a security integration system (SIS). The one or more
(Continued)

tracking systems track movement of individuals throughout the enterprise. The SIS blocks access to the computer resources based on the tracked movement of the individuals within the enterprise.

12 Claims, 4 Drawing Sheets

(51) Int. Cl.
| | | |
|---|---|---|
| A61B 5/16 | (2006.01) | |
| G06Q 10/0631 | (2023.01) | |
| G06Q 10/105 | (2023.01) | |
| G06Q 10/1093 | (2023.01) | |
| G06V 40/16 | (2022.01) | |
| G07C 9/00 | (2020.01) | |
| G07C 9/25 | (2020.01) | |
| G07C 9/30 | (2020.01) | |
| G07C 9/37 | (2020.01) | |
| G08B 13/196 | (2006.01) | |
| H04N 7/18 | (2006.01) | |
| H04W 4/02 | (2018.01) | |
| H04W 4/029 | (2018.01) | |
| G06Q 50/26 | (2012.01) | |

(52) U.S. Cl.
CPC ....... *G06Q 10/0631* (2013.01); *G06Q 10/105* (2013.01); *G06Q 10/1093* (2013.01); *G06V 40/166* (2022.01); *G06V 40/172* (2022.01); *G07C 9/00904* (2013.01); *G07C 9/257* (2020.01); *G07C 9/30* (2020.01); *G07C 9/37* (2020.01); *G08B 13/19608* (2013.01); *H04L 63/105* (2013.01); *H04N 7/181* (2013.01); *H04W 4/023* (2013.01); *H04W 4/029* (2018.02); *A61B 2503/24* (2013.01); *G06Q 50/26* (2013.01); *G06V 40/16* (2022.01); *G06V 40/174* (2022.01)

(58) Field of Classification Search
CPC ...... G07C 9/37; G07C 9/257; G07C 9/00904; G06V 20/52; G06V 40/172; G06V 40/166; G06V 40/174; G06V 40/16; A61B 5/1176; A61B 5/165; A61B 2503/24; G06Q 10/0631; G06Q 10/105; G06Q 10/1093; G06Q 50/26; G08B 13/19608
See application file for complete search history.

(56) References Cited

U.S. PATENT DOCUMENTS

| | | |
|---|---|---|
| 7,921,036 B1 | 4/2011 | Sharma et al. |
| 8,219,438 B1 | 7/2012 | Moon et al. |
| 9,711,034 B2 | 7/2017 | Daniel |
| 9,858,632 B1 | 1/2018 | Shipman et al. |
| 9,996,736 B2 | 6/2018 | Smith et al. |
| 10,033,965 B1 | 7/2018 | Clements et al. |
| 10,109,171 B1 | 10/2018 | M A M et al. |
| 10,121,070 B2 | 11/2018 | Derenne et al. |
| 10,176,513 B1 | 1/2019 | Koka et al. |
| 10,716,473 B2 | 7/2020 | Greiner |
| 10,732,722 B1 | 8/2020 | Heraz |
| 10,755,540 B1 | 8/2020 | Kocher |
| 11,176,357 B2 | 11/2021 | Wang et al. |
| 2002/0083025 A1 | 6/2002 | Robarts et al. |
| 2002/0132663 A1 | 9/2002 | Cumbers |
| 2002/0191817 A1 | 12/2002 | Sato et al. |
| 2003/0210139 A1 | 11/2003 | Brooks et al. |
| 2003/0217024 A1 | 11/2003 | Kocher |
| 2004/0210159 A1 | 10/2004 | Kibar |
| 2004/0234108 A1 | 11/2004 | Li et al. |
| 2005/0075116 A1 | 4/2005 | Laird et al. |
| 2005/0091338 A1* | 4/2005 | de la Huerga ........... G07C 9/28 709/217 |
| 2005/0284200 A1* | 12/2005 | Moon ................ E05B 47/0673 70/278.2 |
| 2006/0024020 A1 | 2/2006 | Badawy |
| 2006/0149589 A1 | 7/2006 | Wager |
| 2006/0190419 A1 | 8/2006 | Bunn et al. |
| 2008/0033752 A1 | 2/2008 | Rodgers |
| 2008/0091515 A1 | 4/2008 | Thieberger et al. |
| 2009/0328152 A1 | 12/2009 | Thomas et al. |
| 2010/0057592 A1* | 3/2010 | Moir ................. G06Q 10/0832 340/572.1 |
| 2010/0153146 A1 | 6/2010 | Angell et al. |
| 2010/0169134 A1 | 7/2010 | Cheng et al. |
| 2010/0245536 A1 | 9/2010 | Huitema et al. |
| 2011/0091847 A1 | 4/2011 | Carroll et al. |
| 2011/0134214 A1 | 6/2011 | Chen et al. |
| 2011/0134240 A1 | 6/2011 | Anderson et al. |
| 2011/0202595 A1 | 8/2011 | Kakiuchi |
| 2012/0262296 A1 | 10/2012 | Bezar |
| 2013/0012790 A1 | 1/2013 | Horseman |
| 2013/0027561 A1 | 1/2013 | Lee et al. |
| 2013/0101165 A1 | 4/2013 | Rexilius et al. |
| 2013/0144914 A1 | 6/2013 | Libal et al. |
| 2013/0155250 A1 | 6/2013 | Myers et al. |
| 2013/0184592 A1 | 7/2013 | Venetianer et al. |
| 2014/0018059 A1 | 1/2014 | Noonan |
| 2014/0104429 A1 | 4/2014 | Ward et al. |
| 2014/0130076 A1 | 5/2014 | Moore et al. |
| 2014/0139678 A1 | 5/2014 | Moriarty et al. |
| 2014/0207950 A1 | 7/2014 | Badiee et al. |
| 2014/0210617 A1 | 7/2014 | Markwitz et al. |
| 2014/0218164 A1* | 8/2014 | Mahapatra .......... H04L 41/0803 340/5.1 |
| 2014/0244264 A1 | 8/2014 | Thirumalainambi et al. |
| 2014/0266604 A1 | 9/2014 | Masood et al. |
| 2014/0270383 A1 | 9/2014 | Pederson |
| 2014/0278629 A1 | 9/2014 | Stephenson et al. |
| 2014/0307926 A1 | 10/2014 | Murakami et al. |
| 2014/0339430 A1 | 11/2014 | Hillis et al. |
| 2015/0028993 A1* | 1/2015 | Dyk ................. G07C 9/00309 340/5.5 |
| 2015/0193507 A1 | 7/2015 | Rappoport et al. |
| 2015/0193718 A1 | 7/2015 | Shaburov et al. |
| 2015/0213304 A1 | 7/2015 | Passe |
| 2015/0278585 A1 | 10/2015 | Laksono et al. |
| 2016/0078279 A1 | 3/2016 | Pitre et al. |
| 2016/0104175 A1 | 4/2016 | Fanourgiakis et al. |
| 2016/0110591 A1 | 4/2016 | Smith et al. |
| 2016/0150124 A1 | 5/2016 | Panda et al. |
| 2016/0170998 A1 | 6/2016 | Frank et al. |
| 2016/0189149 A1 | 6/2016 | MacLaurin et al. |
| 2016/0196728 A1 | 7/2016 | Suman et al. |
| 2016/0203699 A1 | 7/2016 | Mulhern et al. |
| 2016/0217345 A1 | 7/2016 | Appel et al. |
| 2016/0267760 A1 | 9/2016 | Trani |
| 2016/0302711 A1 | 10/2016 | Frank et al. |
| 2016/0330217 A1 | 11/2016 | Gates |
| 2016/0335870 A1 | 11/2016 | Yum |
| 2016/0379046 A1 | 12/2016 | Crandall et al. |
| 2016/0379145 A1 | 12/2016 | Valentino, III et al. |
| 2017/0046496 A1 | 2/2017 | Johnstone et al. |
| 2017/0046566 A1 | 2/2017 | Smith et al. |
| 2017/0061202 A1* | 3/2017 | Shreve ................. G06V 40/176 |
| 2017/0083757 A1 | 3/2017 | Enomoto et al. |
| 2017/0148241 A1 | 5/2017 | Kerning et al. |
| 2017/0169284 A1 | 6/2017 | Chu et al. |
| 2017/0192994 A1 | 7/2017 | Hong et al. |
| 2017/0236029 A1 | 8/2017 | Howell |
| 2017/0236397 A1 | 8/2017 | Myslenski et al. |
| 2017/0255880 A1 | 9/2017 | Daher et al. |
| 2017/0280100 A1 | 9/2017 | Hodge |
| 2017/0294063 A1 | 10/2017 | Hodge |
| 2017/0311863 A1 | 11/2017 | Matsunaga |
| 2017/0351909 A1 | 12/2017 | Kaehler |
| 2017/0357846 A1 | 12/2017 | Dey et al. |
| 2018/0047230 A1 | 2/2018 | Nye |

(56) References Cited

U.S. PATENT DOCUMENTS

| | | | |
|---|---|---|---|
| 2018/0060157 A1 | 3/2018 | Packham et al. | |
| 2018/0069311 A1* | 3/2018 | Pallas | H01Q 7/00 |
| 2018/0069975 A1* | 3/2018 | Honda | H04N 1/00976 |
| 2018/0108192 A1 | 4/2018 | Ho et al. | |
| 2018/0114238 A1 | 4/2018 | Treiser | |
| 2018/0124242 A1 | 5/2018 | Zimmerman | |
| 2018/0154260 A1 | 6/2018 | Sawaki | |
| 2018/0184959 A1 | 7/2018 | Takahashi | |
| 2018/0300557 A1 | 10/2018 | Rodenas et al. | |
| 2018/0308130 A1 | 10/2018 | Hafeez et al. | |
| 2018/0336575 A1 | 11/2018 | Hwang et al. | |
| 2019/0005841 A1 | 1/2019 | Loi et al. | |
| 2019/0043207 A1 | 2/2019 | Carranza et al. | |
| 2019/0050955 A1 | 2/2019 | Beaudet et al. | |
| 2019/0059725 A1 | 2/2019 | Greiner | |
| 2019/0073885 A1 | 3/2019 | Bess et al. | |
| 2019/0080274 A1 | 3/2019 | Kovach et al. | |
| 2019/0110727 A1 | 4/2019 | Egi et al. | |
| 2019/0122082 A1* | 4/2019 | Cuban | G06T 7/73 |
| 2019/0147676 A1 | 5/2019 | Madzhunkov et al. | |
| 2019/0239795 A1 | 8/2019 | Kotake et al. | |
| 2019/0279445 A1 | 9/2019 | Gallagher et al. | |
| 2020/0005416 A1 | 1/2020 | Wade | |
| 2020/0074156 A1 | 3/2020 | Janumpally et al. | |
| 2020/0082438 A1 | 3/2020 | Tunstall | |
| 2020/0125838 A1 | 4/2020 | Dalley, Jr. et al. | |
| 2020/0234523 A1 | 7/2020 | Ma et al. | |
| 2020/0256113 A1 | 8/2020 | Salter et al. | |
| 2020/0302187 A1 | 9/2020 | Wang et al. | |
| 2020/0302715 A1 | 9/2020 | Tulsidas | |
| 2020/0334344 A1 | 10/2020 | Schwartz et al. | |
| 2020/0344238 A1 | 10/2020 | Ainsworth et al. | |
| 2021/0042527 A1 | 2/2021 | Ton-That | |
| 2021/0182542 A1 | 6/2021 | Lau | |
| 2021/0185276 A1 | 6/2021 | Peters et al. | |
| 2021/0196169 A1 | 7/2021 | Ainsworth et al. | |
| 2021/0201269 A1 | 7/2021 | Ainsworth et al. | |
| 2021/0202067 A1 | 7/2021 | Williams et al. | |
| 2021/0248541 A1 | 8/2021 | Heier | |
| 2021/0298157 A1* | 9/2021 | Olaleye | H05B 47/155 |
| 2021/0374391 A1 | 12/2021 | Jorasch et al. | |
| 2021/0374426 A1 | 12/2021 | Park et al. | |
| 2022/0207915 A1 | 6/2022 | Voss | |
| 2022/0329589 A1 | 10/2022 | Buscemi et al. | |
| 2022/0382840 A1 | 12/2022 | Weston et al. | |

FOREIGN PATENT DOCUMENTS

| | | |
|---|---|---|
| DE | 102016000091 A1 | 7/2017 |
| JP | 2017033244 A | 2/2017 |
| JP | 2017073107 A | 4/2017 |
| JP | 2018138155 A | 9/2018 |
| JP | 6752819 B2 | 9/2020 |
| WO | 2013166341 A1 | 11/2013 |
| WO | WO 2016128842 | 8/2016 |
| WO | 2018096294 A1 | 5/2018 |

OTHER PUBLICATIONS

International Search Report and Written Opinion of the International Searching Authority, mailed on Jan. 4, 2019, from International Application No. PCT/US2018/058976, filed on Nov. 2, 2018. 13 pages.

International Search Report and Written Opinion of the International Searching Authority, mailed on Dec. 21, 2018, from International Application No. PCT/US2018/058984, filed on Nov. 2, 2018. 14 pages.

International Search Report and Written Opinion of the International Searching Authority, mailed on Dec. 21, 2018, from International Application No. PCT/US2018/058996, filed on Nov. 2, 2018. 14 pages.

International Preliminary Report on Patentability, mailed on May 14, 2020, from International Application No. PCT/US2018/058971, filed on Nov. 2, 2018. 7 pages.

International Preliminary Report on Patentability, mailed on May 14, 2020, from International Application No. PCT/US2018/058976, filed on Nov. 2, 2018. 8 pages.

International Preliminary Report on Patentability, mailed on May 14, 2020, from International Application No. PCT/US2018/058984, filed on Nov. 2, 2018. 9 pages.

International Preliminary Report on Patentability, mailed on May 14, 2020, from International Application No. PCT/US2018/058996, filed on Nov. 2, 2018. 9 pages.

Turner, A., "Biometrics in Corrections: Current and Future Deployment," Corrections Today, 62-64 (2003).

Miles, A. C., et al., "Tracking Prisoners in Jail with Biometrics: An Experiment in a Navy Brig," NIJ Journal, 253: 1-4 (2006).

Miles, Christopher A. Cohn, Jeffrey P. Tracking Prisoners in Jail With Biometrics: An Experiment in a Navy Brig. National Institute of Justice. (Year: 2006).

Turner, Allan. Biometrics in Corrections: Current and Future Deployment. Corrections Today. (Year: 2003).

S. Mora, V. Rivera-Pelayo and L. Muller, "Supporting mood awareness in collaborative settings," 7th International Conference on Collaborative Computing: Networking, Applications and Worksharing (CollaborateCom), 2011, pp. 268-277, doi: 10.4108/icst.collaboratecom.2011.247091. (Year: 2011).

M. Mumtaz and H. Habib, Evaluation of Activity Recognition Algorithms for Employee Performance Monitoring. Pakistan, 2012. (Year: 2012).

H. Gunes, B. Schuller, M. Pantie and R. Cowie, "Emotion representation, analysis and synthesis in continuous space: A survey," 2011 IEEE International Conference on Automatic Face & Gesture Recognition (FG), Santa Barbara, CA, USA, 2011, pp. 827-834, doi: 10.1109/FG.2011.5771357. (Year: 2011).

Anonymous, "Real-Time Optimization of Employee Productivity using Workplace Mood Analysis," IP.com Prior Art Database Technical Disclosure, Feb. 18, 2016, 5 pages.

Seddigh et al., "Does Personality Have a Different Impact on Self-Rated Distraction, Job Satisfaction, and Job Performance in Different Office Types?", PLoS One, May 25, 2016, 11 (5):e0155295, pp. 1-14.

Lutchyn, Y., et al., "MoodTracker: Monitoring collective emotions in the workplace," 2015 International Conference on Affective Computing and Intelligent Interaction (ACII), 295-301 (2015).

Sidhu, R.S., et al., "Smart surveillance system for detecting interpersonal crime," International Conference on Communication and Signal Processing (ICCSP), 2003-2007 (2016).

Noma-Osaghae et al., "Design and Implementation of an Iris Biometric Door Access Control System", 2017, 2017 International Conference on Computational Science and Computational Intelligence (CSCI), 4 pages.

Moseley et al., "Access Control and Monitoring in a Prison Environment", 1998, Proceedings IEEE 32nd Annual 1998 International Carnahan Conference on Security Technology (Cat. No. 98CH36209), 5 pages.

* cited by examiner

METHODS AND SYSTEM FOR CONTROLLING ACCESS TO ENTERPRISE RESOURCES BASED ON TRACKING

RELATED APPLICATIONS

This application is a § 371 National Phase Application of International Application No. PCT/US2018/058971, filed on Nov. 2, 2018, now International Publication No. WO 2019/090087, published on May 9, 2019, which International Application claims the benefit under 35 USC 119 (e) of U.S. Provisional Application No. 62/581,207, filed on Nov. 3, 2017, both of which are incorporated herein by reference in their entirety.

BACKGROUND OF THE INVENTION

Enterprises, such as private and public companies, municipal, state and federal governmental agencies, and other entities, will often maintain a number of disparate systems to support their operations, track their business relationships, and maintain security. Enterprise Resource Planning (ERP) systems are computer systems that allow enterprises to manage operations. Employee Resource Management (ERM) systems are typically different computer systems that allow the enterprises to track, schedule, and pay their employees. Access control systems are principally concerned with physical security and the selective access to, restriction of access to, and/or notification of access to the enterprises' buildings and/or secured parts of those buildings. Information technology (IT) security systems are principally concerned with control and restricting access to computer resources, often including access to any ERP or ERM systems, and possibly other systems such as file servers, etc. In addition, other security systems are often employed by the enterprises to round-out their security needs. A common example is a surveillance system, which may be integrated with any access control system to varying degrees.

The ERM systems store and manage many different types of information associated with employees. The ERM system might execute on a single computer system or server, or across multiple computer systems and servers, or be implemented in a cloud-based computer system. The different types of employee information often controlled and managed by the ERM systems include biographic, including demographic, information, payroll and salary information, job performance and attendance information, benefits information, and training and compliance information, to list some common examples.

Modern ERM systems typically encompass the functionality of multiple legacy systems that had separately managed and stored the different types of information associated with the employees. These legacy systems might have had separate payroll systems for the payroll and salary information, human resources systems for the biographic, job performance and attendance information, benefits systems for the benefits information, and learning systems for the training and compliance information, in examples. At the same time, the ERM system can simply be a collection of local or remote databases that store the different types of information associated with each employee.

ERP systems generally track business resources such as cash, raw materials, and production capacity. The ERP systems can track business commitments such as orders, purchase orders, and possibly might overlap with ERM systems. As such, these ERP systems are computer systems that often include computer databases and database management systems for the databases, along with different user interfaces. The different user interfaces allow the operators to obtain information from the systems and submit information to them. The ERP systems typically further include various computer systems connected with manufacturing and the control and management of other operations of the enterprises.

IT security systems can take many forms. They will often include asset management database computer systems that allow the enterprises to track their computers, the status of the computers, individuals to whom the computers are assigned, along with other systems such as servers, cloud server systems, and networking devices, to list some examples. The IT security systems will almost always include one or more authentication server systems. These computers provide network services that computer systems and applications that execute on those computer systems use to authenticate the credentials, usually account names and passwords, of their users. For example, when a client computer successfully submits a valid set of credentials that were entered by a user trying to log onto the computer, the client computer receives a cryptographic ticket that it can subsequently use to access various other systems such as the enterprise's ERP systems, ERM systems and other computers systems such as even mundane file servers.

The access control systems typically include access control readers. These readers are often installed at access points of the buildings to control access to restricted areas, such as buildings or areas of the buildings. Examples of access points include front and interior doors of a building, elevators, hallways connecting two areas of a building, to list a few examples. The access control readers authenticate identities of (or authorize) individuals and then permit those authenticated individuals to access the restricted areas through the access points. Typically, individuals interact with the access control readers by swiping keycards or bringing contactless smart cards within range (approximately 2-3 inches or 5 centimeters) of a reader. The access control readers read user information of the keycards, such as credentials of the individuals, and then the access control systems determine if the individuals are authorized to access the restricted areas. If the individuals are authorized to enter the restricted areas, then the access control readers allow access to the restricted areas by unlocking locked doors, signaling that doors should be unlocked, or generating alarms upon unauthorized entry, for example.

More recently, frictionless access control systems are being proposed and designed. These systems typically rely on individuals carrying beacon devices that can broadcast credentials, such as dedicated fob devices or personal mobile computing devices such as tablet or smart phone computing devices. These systems are "frictionless" in that the individual may not have made any overt gesture indicating a desire to access the restricted area, e.g., the individuals did not swipe a keycard. The access control systems will then monitor and track the individuals as they move through the buildings and automatically open access points such as doors when approached, assuming that the individuals are authorized to pass through those access points.

Enterprise surveillance systems are used to help protect people, property, and reduce crime. These systems are used to monitor buildings, lobbies, entries/exits, and secure areas within the buildings of the enterprises, to list a few examples. The surveillance systems record illegal activity such as theft or trespassing, in examples. At the same time, these surveillance systems can also have business uses. They can track employee locations across different rooms within buildings and among the different buildings of the enterprises.

In these surveillance systems, surveillance cameras capture image data of scenes. The image data is typically represented as two-dimensional arrays of pixels. The cameras then include the image data within streams, and users of the system such as security personnel view the streams on display devices such as video monitors. The image data is also typically stored to a video management system (VMS) for later access and analysis.

Increasingly, it is being proposed to make these VMSs smarter. For example, VMSs with image analytics systems are becoming more prevalent. These analytics systems allow the VMSs to interpret the captured image data and possibly send alerts when detecting trespassing or other problems. One common type of image analytics is facial recognition. In such instances, modules of the VMS will identify faces within the image data and compare those faces to databases to try to identify the different individuals captured in the image data.

SUMMARY OF THE INVENTION

A proposed enterprise security system obtains information from disparate repositories and combines the information with tracking information to validate movement of individuals within the enterprise and also uses the information to validate log-on events on computer systems. In one application, the enterprise security system uses the combined information to determine whether the individuals are located in and/or moving to a correct/authorized location for those individuals. For example, based upon a desk location, it will be possible to monitor the location of an individual within a building and determine that they are in and/or are moving to the correct location within the building.

Additional functions are possible. The system can use biographic and physical information such as age, gender, facial hair, and whether or not the person is wearing glasses, in examples, to determine that obtained facial recognition information matches that of an employee record maintained by the ERM system. The system can combine facial recognition with information technology (IT) systems monitoring to confirm that a person whose face has been recognized uses the correct login identifier to log into a computer system within the building(s) of the enterprise.

In general, according to one aspect, the invention features an enterprise security system. The system includes one more tracking systems, an IT system and a security integration system. The one or more tracking systems track movement of the individuals throughout the enterprise. The IT system provides access to computer resources within the enterprise. The security integration system can then generate commands to block access to the computer resources based on the tracked movement of the individuals within the enterprise.

In this way, the system might augment the validation provided by a traditional authentication server by ensuring that log-on attempts are consistent with the individuals actually present in a conference room, for example.

In embodiments, the tracking systems include a surveillance system including surveillance cameras and a facial recognition module for performing facial recognition of individuals in the image data from the surveillance cameras. The tracking systems can also, or alternatively, include access control systems that control access of individuals through access points within the enterprise.

Typically, the security integration system determines authorized computer systems for individuals and instructs the IT system to block access to the computer systems when authorized users of the computer systems are not present. The security integration system can also access an asset management database to determine locations of the computer systems within the enterprise.

In general, according to another aspect, the invention features an enterprise security system. The enterprise security system includes one or more tracking systems for tracking movement of individuals throughout an enterprise, an employee resource management system including an employee database, and a security integration system. The employee database stores location of desks of the employees. The security integration system receives a metadata stream of the tracked movement of the employees and determines whether the employees are moving to and/or from the respective desks of the employees by reference to the information from the employee database.

In general, according to yet another aspect, the invention features an enterprise security method. The method includes tracking movement of individuals throughout an enterprise, providing access to computer resources within the enterprise using an authentication server, and blocking access to the computer resources based on the tracked movement of the individuals within the enterprise.

In one example, tracking movement includes controlling and reporting access of individuals through access points within the enterprise. Tracking movement can further or alternatively include capturing images of the individuals and performing facial recognition of the individuals.

In general, according to still another aspect, the invention features another enterprise security method. This method includes tracking movement of individuals throughout an enterprise, an employee resource management system including an employee database indicating location of desks of the employees, and receiving a metadata stream of the tracked movement of the employees and determining whether the employees are moving to and/or from the respective desks of the employees.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
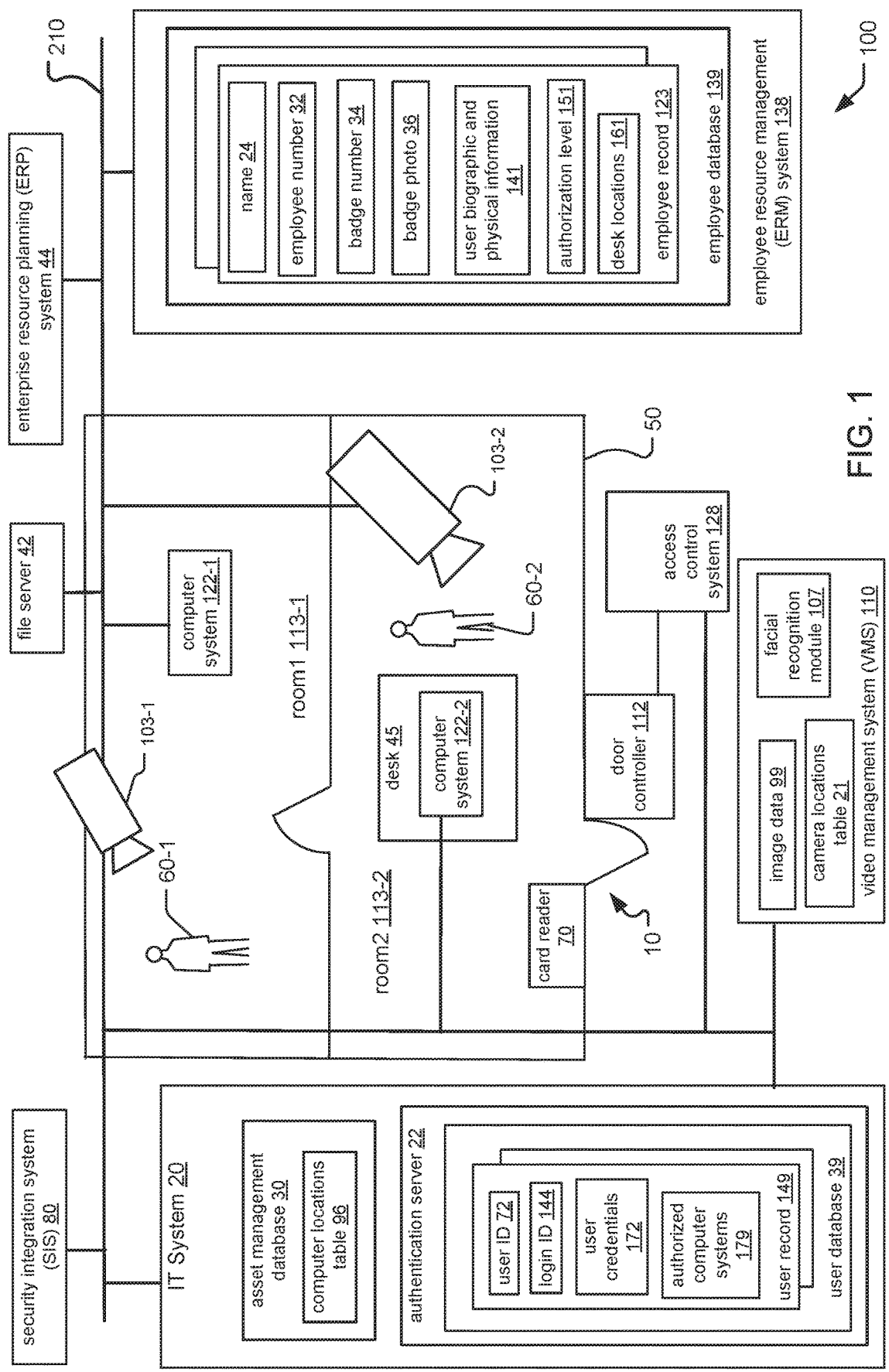
FIG. 1 is a schematic diagram showing rooms of a building and an enterprise security system installed at the building, in accordance with principles of the present invention.

FIG. 1 shows an exemplary enterprise including an enterprise security system 100, which has been constructed according to the principles of the present invention.

The figure shows client computer systems 122 at a building 50 of the enterprise. Some of these client computer systems might be public terminals in conference rooms that might be used by different individuals over the course of the day. In other examples, the client computer systems 122 are dedicated computer systems assigned to a specific employees of the enterprise or shared computers systems such as servers or server systems.

Also shown are other computer systems that are associated with the operations of the enterprise, such an enterprise information technology (IT) system 20, a surveillance system, an ERM system 138, a file server 42, an access control system 128, and an ERP system 44. Finally, a security integration system (SIS) 80 provides some of the important functions of the present invention. A local area or enterprise network 210 provides network connectivity.

In more detail, the cameras 103 of the surveillance system capture image data 99 of the rooms 113 throughout the enterprise's building and thus images of individuals 60 in each room 113. Cameras 103-1 and 103-2 are respectively installed in rooms 113-1 and 113-2.

The surveillance system's VMS 110 stores the image data 99 from the cameras 103 and includes a camera locations table 21 and a facial recognition module 107. The camera locations table 21 typically has a record for each of the surveillance cameras 103. The record contains such information as the room in which the camera is installed. It may also include information concerning the type of camera and possibly even the field of view of the camera with respect to a map or floor layout of the building 50. The facial recognition module 107 determines facial recognition information of the individuals captured in the image data and monitors movement and/or activity of individuals 60 within the rooms 113.

The IT system 20 includes an authentication server 22. The authentication server 22 allows the individuals 60 to log onto the computer systems 122, such as client computer systems, and then typically access other resources such as the file server 42 and/or the ERP system 44 and/or ERM system 138. For this purpose, the authentication server 22 has a user database 39 that stores user records 149 for the individuals 60. The individuals 60 are typically employees of the enterprise. Each user record 149 includes information that identifies each individual and the computer systems 122 each is authorized to access, in examples. In more detail, the user record 149 for each individual 60 typically includes a user ID 72, a login ID 144, user credentials including passwords 172, and a list of authorized computer systems 179.

Another common feature of IT systems is an asset management database 30. The asset management database 30 includes a computer locations table 96. As its name implies, the table 96 maintains locations (e.g. room numbers) for each of the computer systems 122. Often, these asset management databases 30 will include additional information such as specific details concerning the computer systems 122, such as production year operating system, applications installed on the computer systems and possibly other license information.

The ERM system 138 is preferably as described hereinabove. As such, it has an employee database 139 that stores employee records 123 of employees 60. The employee records 123 include information for identifying each employee and locations of desks 45 within the building 50 for the employees. In more detail, each employee record 123 typically includes a name 24, an employee number 32, a badge number 34, a badge photo 36, user biographic and physical information 141, an authorization level 151, and one or more desk locations 161. The desk locations 161 list the locations of desks that each employee is authorized to be present at or is otherwise expected to be near during work hours. In addition, the ERM system 138 may also include other information such as databases that store the same information for contractors and visitors to the enterprise.

The user biographic and physical information 141 includes other information for possibly identifying each individual 60. This information might include the following: a birthplace, home address, age, race, hair color/length, and whether the individual typically wears glasses, in examples.

The access control system 128 controls physical access through access points 10 of the building 50. In the illustrated example, the access points are doors, but may also include hallways or elevators or floors within the buildings of the enterprise. Typically, the access control system 128 further includes card readers for reading employee badges and/or frictionless readers that might validate employees based on credentials provided by a mobile computing device such as a smart phone operated by the employees. In this way, the access control system is able to monitor movement of individuals through access points.

In one embodiment, the enterprise security system includes one or more tracking systems (such as the surveillance system and/or the access control system). These one or more tracking systems track movement of the individuals 60 throughout the enterprise and provide this information as meta data streams. The IT system 20 provides access to computer resources within the enterprise and provides its own meta data stream of log-on events.

The SIS 80 functions to integrate the operation of the tracking system(s) and the IT system. As such, the SIS 80 can be a separate computer system or could be a process or module that executes on the IT system computers, e.g., authentication server, or on a computer associated with the tracking systems, or even a separate computer system or a computer system integrated with the ERP or ERM computer systems. In any case, the SIS instructs the IT system 20 to block access to the computer systems 122 when authorized users of the computer systems 122 are not present.

In the illustrated example, the computer systems 122 are located in the rooms 113. Room 111-1 includes computer system 122-1. Room 113-2 includes computer system 122-2 upon a desk 45. The locations and types of there computers are stored in the computer locations table 96 of the asset management database 30. Multiple individuals 60 are located within and/or are moving about the rooms 113, and are attempting to access computer resources from within the rooms 113. Individual 60-1 is located in room1 113-1 and individual 60-2 is located in room2 113-2. Individual 60-2 is also located near the desk 45 and is attempting to access/log onto a user account via the computer system 122.

In general, the individuals 60 might be employees. As such, when the individuals are originally hired as employees, a guard or security operator or human resources representative would create the employee record 123 for each employee in the employee database 139. The security operator also takes a picture of the employee's face to use as the badge photo 36, and additionally uses the facial recognition module 107 of the VMS 110 to create stored facial recognition information for each of the employees.

The facial recognition information can be of different types. In one example, the information is a biometric identifier such as a facial signature of the individual. In another example, the information is simply a still image of the person's face extracted from the image data, also known as a facial patch.

The facial signature for an individual is a unique value or set of values that represent the face of an individual/employee. The facial recognition module 107 uses one or various predetermined facial signature algorithms to create the facial signature, based upon various features of each person's face. These features include the eyes, nose, mouth, eyebrows, cheekbones, and chin of each face, and distances between each of these features, in examples.

The facial recognition module also maps each instance of facial recognition information (e.g. the facial signature or facial patch) for each employee to a user credential or other identifier (OD). In this way, the OD associated with each instance of stored facial recognition information can be used to identify the individual for which the facial signature was obtained.

The VMS 110 then stores the facial recognition information and associated ID for identifying each employee. In one example, the VMS stores this information locally to the VMS 110. In another example, the VMS 110 might store this information to the employee record 123 for each employee.

The enterprise security system 100 generally operates as follows. After the individuals 60 are registered as employees, one or more individuals arrive at access points 10 such as doors of the building 50. The individuals typically present keycards that include their user credentials to the card readers 70 of the access control system 128 at the doors. The cameras 103 also capture and send the image data 99 of the individuals to the VMS 110.

The VMS 110 then uses its facial recognition module 107 to determine whether the images of the individuals 60 in the image data 99 from the surveillance cameras match the stored facial recognition information for registered employees. If the individuals 60 are determined to be employees, the VMS 110 operates in conjunction with the SIS 80, the IT system 20, the ERM 138, and possibly the ERP system 44 to determine whether the individuals are: in the correct rooms within the building 50; attempting to access computer systems to which they are authorized; and traversing paths near desk locations to which they are assigned, in examples.

Figure 2A:
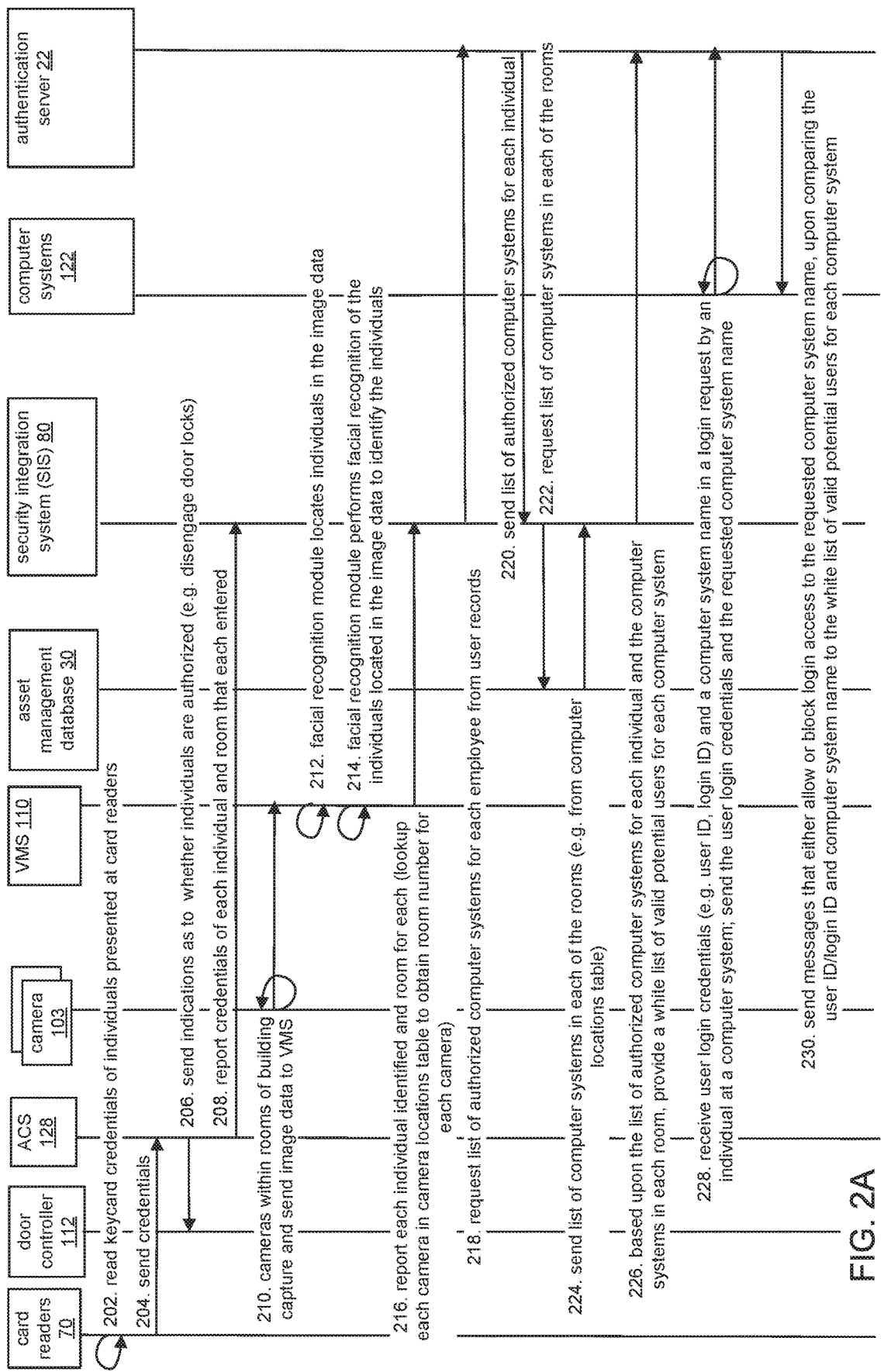
FIG. 2A is a sequence diagram that illustrates one method of operation for the enterprise security system in FIG. 1, where the method determines whether an otherwise authorized individual, at a computer system in a room within the building, is authorized to log into a computer system within the building.

FIG. 2A is a sequence diagram that illustrates one application of the enterprise security system 100.

The enterprise security system 100 protects against improper access of computer systems 122 within the rooms 113 of the building. After the identity of the individual 60 entering or within a room 113 has been determined via facial recognition, only IT user records 149 associated with that individual will be allowed to be accessed from computer systems located within that room 113. Thus, if an otherwise authorized user 60 enters the room 113 and tries to use another person's credentials, the individual 60 will be prohibited from doing so. In this way, only an individual 60 that is expected to be near a computing system 122 at a specific location can log onto that computer system 122, in one example.

In more detail, in step 202, one or more card readers 70 read keycard credentials of individuals 60 presented at the card readers. The card readers 70 send the credentials to the ACS 128 in step 204.

According to step 206, the ACS 128 sends an indication as whether the individuals 60 are authorized. In one example, the indication is a door lock signal to unlock or otherwise disengage the door locks for the doors (or other access points) at which the card readers 70 are installed. The ACS 128 sends these indications to the door controller 112. Then, in step 208, the ACS 128 reports these credentials of the individuals 60 and the room 113 that each entered to the SIS 80 as an access control meta data stream.

At the same time, in step 210, the cameras 103-1 and 103-2 within the rooms 113-1 and 113-2 of the building 50 capture the image data 99 of scenes in the rooms 113. The cameras 103 send the image 99 to the VMS 110 for storage and subsequent analysis.

In step 212, the facial recognition module 107 of the VMS 110 locates the individuals 60 in the image data 99. In step 214, the facial recognition module 107 then performs facial recognition of the individuals located in the image data 99 to identify the individuals 60. For this purpose, the facial recognition module 107 preferably uses the same facial recognition algorithms used when the security operators first registered the individuals as employees. In this way, the facial recognition module 107 can identify employees in the image data by reference to the badge photos 36 stored in the employee database 139 of the ERM system 138.

It can also be appreciated that the facial recognition module 107 can be included within and execute upon other components of the enterprise management system 100. In one example, the facial recognition module 107 might be integrated within the cameras 103 and execute upon a microcontroller of the cameras 103. In another example, the facial recognition module 107 might execute upon a microcontroller or central processing unit (CPU) of the ACS 128.

In step 216, the VMS 110 provides a surveillance meta data stream of the identified individuals, using facial recognition, and the rooms 113 in which those individuals are located based on the location of the various cameras 103 that captured their image, along with a timestamp indicating the time of identification. For this purpose, the VMS 110 executes a lookup of a camera identifier for each camera 103 in the camera locations table 21 to obtain the location (e.g. room number) of each camera 103, The VMS 110 then reports this information in the surveillance system meta data stream, including each identified individual and room and time, to the SIS 80.

At the same time, in step 218, the security integration system 80 requests a list of authorized computer systems 179 for each of the employees from the authentication server 22 of the IT system 20. The authentication server 22 then returns the list of authorized computer systems 179 for each of the employees in step 220.

The SIS 80 further determines the locations of the various computer systems 122 relative to the rooms 113 from the asset management database 30. This is indicated in step 222. For this purpose, the SIS 80 queries the computer locations table 96 of the asset management database 30. The asset management database 30 returns the computer locations relative to the rooms 113 back to the SIS 80 in step 224.

Then, based on the list of authorized computer systems for each individual and the computer systems in each room, the SIS 80 provides a white list of valid potential users, i.e., the valid users that are known to be in the same room as the computer systems, for each computer system 122. The SIS 80 provides the white list to the authentication server 22, in step 226.

The computer systems 122 might then receive user login requests from individuals 60 within the rooms, in step 228. For example, one of the individuals may try to logon to one of the client computers 122 by entering a username and password. The user login requests include at least user credentials (e.g. user ID, login ID) and a computer system name. The computer systems then send the user login requests including the user credentials and the requested computer system names to the authentication system 22 for further processing.

The authentication server 22, in step 230, compares the user credentials and the requested computer system names in the login requests to the white list of valid potential users for each computer system 122. Upon finding a matching entry in the white list for that individual 60, the authentication system 22 authenticates that individual on that computer system and might further send a message to the computer system 122 to allow access to the computer system 122 named in the user login request. Otherwise, the authentication server 22 denies/blocks access to the computer system named in the user login request when it has been determined that the user is not even present in the room, for example.

Figure 2B:
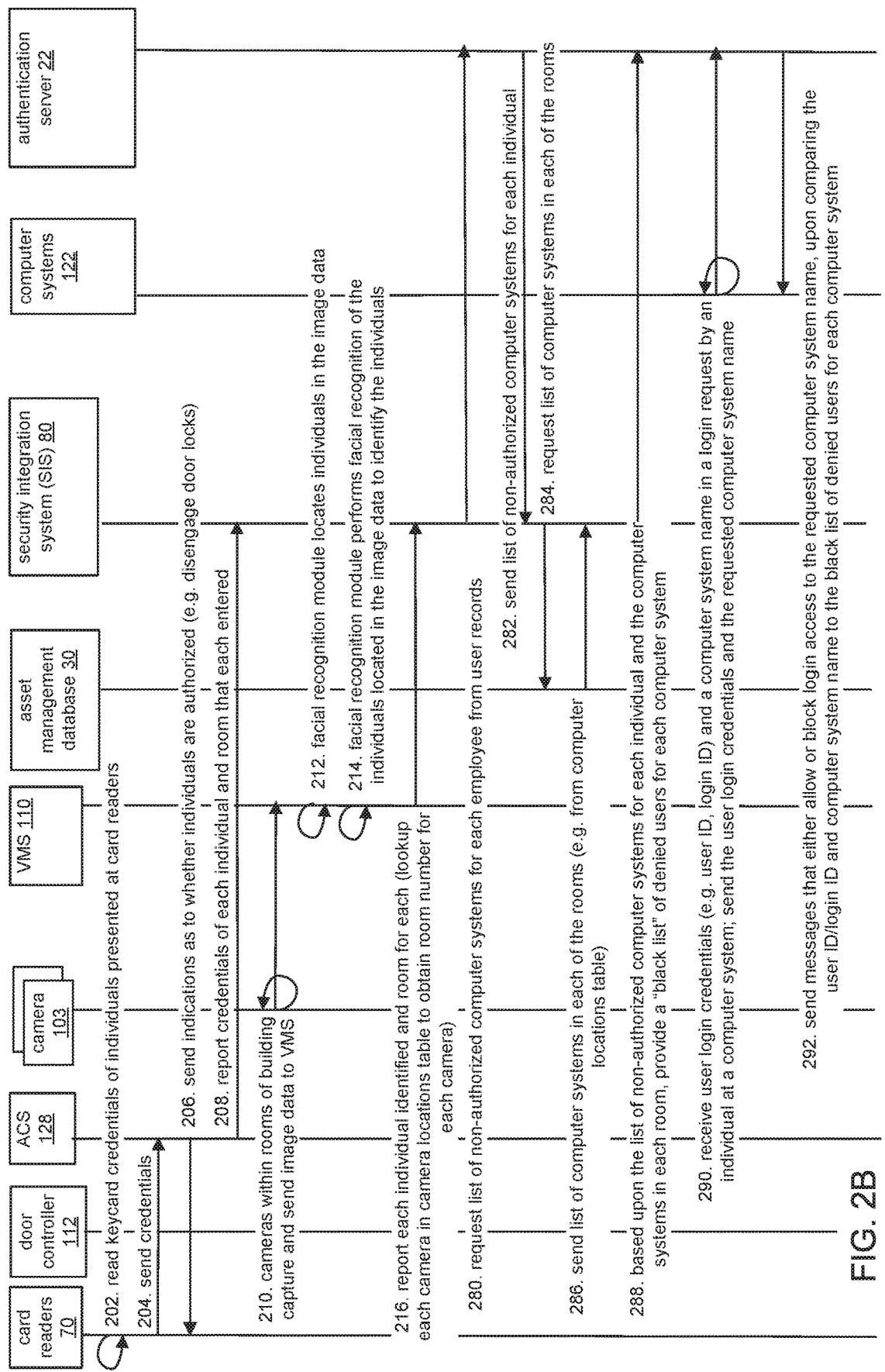
FIG. 2B is a sequence diagram showing another embodiment where the enterprise security system generates a black list.

FIG. 2B is a sequence diagram that illustrates an alternate implementation for the enterprise security system 100.

In FIG. 2B, steps 202 through 216 are substantially similar as steps 202 through 216 in FIG. 2A.

In step 280, the security integration system 80 requests a list of authorized computer systems for each of the employees from the authentication server 22 of the IT system 20. The authentication server 22 then returns the list of authorized computer systems 179 for each of the employees in step 282.

The SIS 80 further determines the locations of the various computer systems 122 relative to the rooms 113 from the asset management database 30. This is indicated in step 284. For this purpose, the SIS 80 requests the computer locations table 96 of the asset management database 30. The asset management database 30 returns the computer locations relative to the rooms 113 back to the SIS 80 in step 286.

Then, based on the list of authorized computer systems for each individual and the computer systems in each room, the SIS 80 provides a black list of denied users for each computer system 122. In step 288, the SIS 80 provides the black list for each of the individuals 60 back to the authentication server 22.

The computer systems 122 then receive user login requests from individuals 60 within the rooms, in step 290. This is substantially similar to step 288 in FIG. 2A. The computer systems 122 then send the user login requests including the user credentials and the requested computer system names to the authentication system 22 for further processing.

The authentication system 22, in step 292, compares the user credentials and the requested computer system names in the login requests to the black list of denied users for each computer system 122. Upon finding a matching entry in the black list for that individual 60, the authentication server 22 blocks access to the computer system 122 named in the user login request.

In this way, the enterprise security system 100 also tracks movement of individuals throughout an enterprise, provides access to computer resources within the enterprise using an authentication server, and blocks access to the computer resources based on the tracked movement of the individuals within the enterprise.

Figure 3:
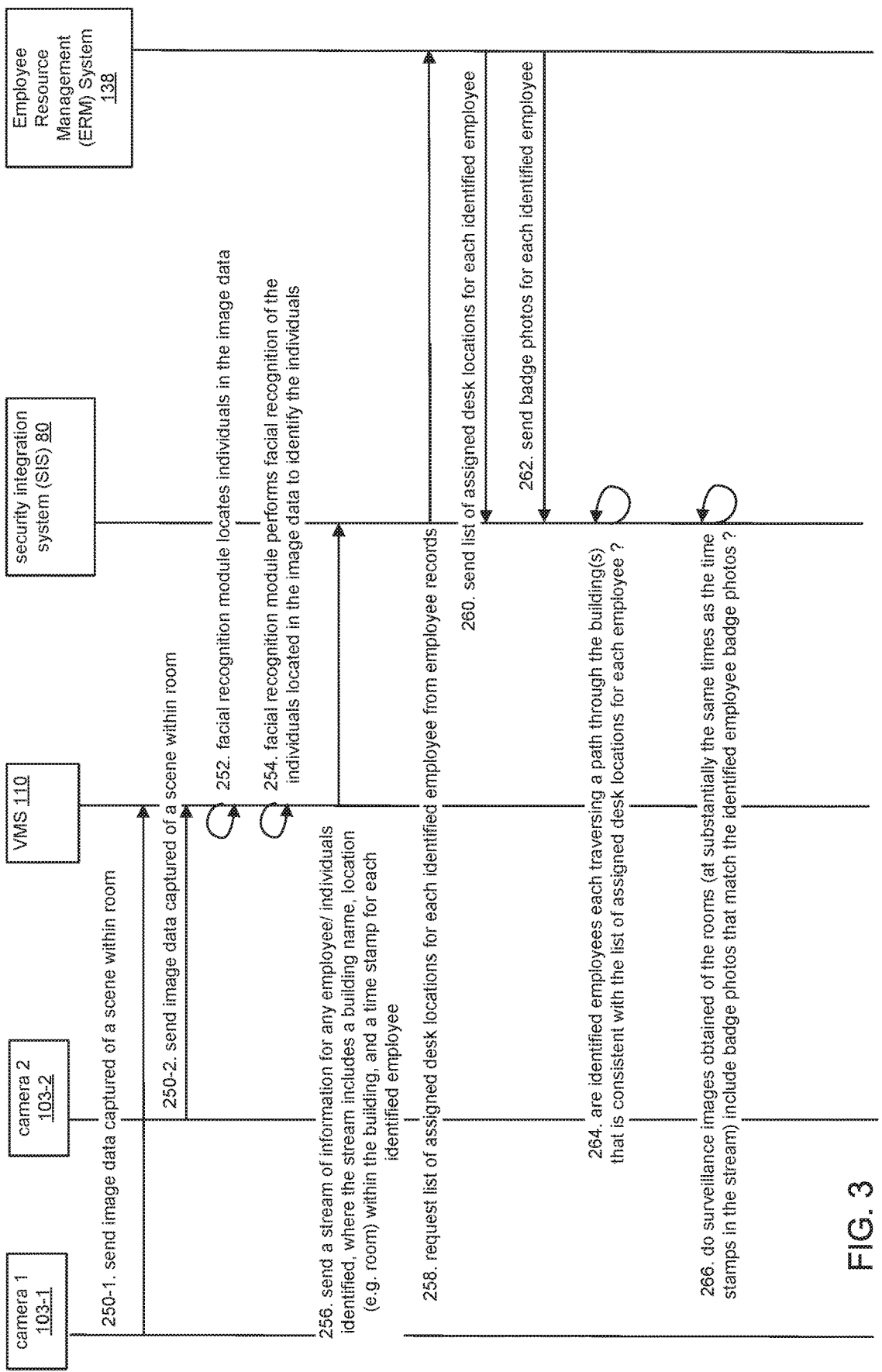
FIG. 3 is a sequence diagram that illustrates another method of operation for the enterprise security system, where the system determines whether an otherwise authorized individual is traversing a path near desk locations to which they are assigned.

FIG. 3 illustrates another method of operation for the enterprise security system 100.

As before, the VMS 110 provides a surveillance metadata stream to the SIS 80. The stream includes identified employees/individuals and location(s) in the building 50 where they were tracked along with a timestamp indicating the time of detection. The ACS 128 provides its access control meta data stream after employees interact with card readers, for example.

Now, the SIS 80 also accesses the ERM system 138 to determine the assigned desks for those employees and then confirms that the employees are on valid paths to or from their desks 45, in one example.

As before, the enterprise security system 100 includes one or more tracking systems for tracking movement of the individuals 60 throughout the enterprise. In this way, the SIS 80 receives a metadata stream of the tracked movements of the employees and determines whether the employees are moving to and/or from the respective desks of the employees by reference to information from the ERM 138.

In more detail, in step 250-1, camera 103-1 sends image data 99 captured of a scene within room 113-1 to the VMS 100. In a similar vein, camera 103-2 in step 250-2 sends image data 99 captured of a scene within room 113-2 to the VMS 110.

In step 252, the facial recognition module 107 of the VMS 110 locates the individuals 60 in the image data 99. The facial recognition module 107 then performs facial recognition of the individuals located in the image data 99 to identify the individuals 60 in step 254.

According to step 256, the VMS 110 sends the metadata stream of information for any employee/individuals 60 identified, where the stream includes a building name, location (e.g. room 113) within the building 50, and a time stamp for each identified employee, in examples, to the SIS 80.

Also, as before, the ACS 128 also preferably provides its access control meta data stream to the SIS 80.

In step 258, the SIS 80 requests a list of assigned desk locations 161 for each identified employee. The desk locations 161 are included in the employee records 123 of the individuals, which the ERM system 138 maintains in its employee database 139. The ERM system 138 sends the list of assigned desk locations 161 for each identified employee back to the SIS 80 in step 260. In addition, the ERM system 138 sends the badge photo 36 for each identified employee to the SIS 80 in step 262.

In step 264, the SIS 80 determines if each of the identified employees are traversing a path through the building(s) 50 that is consistent with the list of assigned desk locations for each employee.

The SIS 80 also determines, in step 266, if surveillance images obtained of the rooms (at substantially the same times as the time stamps in the stream) include badge photos 36 that match the identified employee badge photos. A mismatch indicates that the individuals 60 in the rooms 113 may have stolen or forged their security badges. The SIS 80 can then send messages alerting security operators of this event so that the security operators can investigate further.

The method of operation for the enterprise security system 100 in FIG. 3 has additional benefits. The system might be used to monitor usage of desks 45 by the individuals 60 over time. This could then be provided as input to future real estate occupancy decisions by analyzing the space usage over a longer period. For example, if the occupancy is less than 80% of the available desk 45 space, an operator at the enterprise may wish to consider moving to a smaller building 50. Similarly, if the desk 45 space usage exceeds 90%, then, if the enterprise wishes to expand, it may need to consider moving to a larger building 50.

While this invention has been particularly shown and described with references to preferred embodiments thereof, it will be understood by those skilled in the art that various changes in form and details may be made therein without departing from the scope of the invention encompassed by the appended claims.

What is claimed is:

1. An enterprise security system, comprising:
one or more tracking systems for tracking, using facial recognition to identify individuals based on images captured using one or more surveillance cameras installed in multiple rooms of an enterprise building, movement of the individuals throughout the multiple rooms, wherein the one or more tracking systems include an access control system for controlling physical access of the individuals through access points within the enterprise building, a first access point of the access points permitting physical access to a room of the enterprise building and having a reader device that is included in the access control system;
an information technology (IT) system for providing access to computer resources within the enterprise building; and
a security integration system for one of:
receiving, from the IT system, a list of authorized computers for each of the individuals, and providing, to the IT system based on the list of authorized computers, a white list identifying one or more of the individuals that are determined, based on a metadata stream of the tracked movement of the individuals, to be in a same room as the authorized computers; or
receiving, from the IT system, a list of unauthorized computers for each of the individuals, and providing, to the IT system based on the list of unauthorized computers, a black list identifying one or more the individuals that are determined, based on the metadata stream of the tracked movement of the individuals, to be in a same room as the unauthorized computers;
wherein the metadata stream includes location within the enterprise building and time stamp for each identified individual,
wherein the IT system allows or blocks access, requested by the one or more of the individuals, to at least a portion of the computer resources based on the white list or the black list.

2. The system as claimed in claim 1, wherein the security integration system determines at least the portion of the computer resources as authorized computer systems for the one or more of the individuals identified in the white list, and wherein the IT system blocks access to the authorized computer systems, for one of the individuals that is not identified in the white list.

3. The system as claimed in claim 1, wherein the security integration system accesses an asset management database to determine locations of computer systems within the enterprise building.

4. An enterprise security system, comprising:
one or more tracking systems for tracking, using facial recognition to identify an individual based on images captured using one or more surveillance cameras installed in multiple rooms of an enterprise building, movement of the individual throughout the multiple rooms, wherein the one or more tracking systems include an access control system for controlling physical access of individuals through access points within the enterprise building, a first access point of the access points permitting physical access to a room of the enterprise building and having a reader device that is included in the access control system;
an employee resource management system including an employee database indicating location of a desk of the individual;
a security integration system for determining, based on receiving a metadata stream of the tracked movement of the individual, whether the individual is moving to and/or from the desk of the individual, wherein the metadata stream includes location within the enterprise building and time stamp for the individual;
providing, based on a list of authorized computer resources, a white list identifying the individual determined, based on the metadata stream, to be moving to the desk of the individual associated with the authorized computer resources; and providing, based on the white list, access for the individual to the authorized computer resources.

5. A method, comprising:

tracking, using facial recognition to identify an individual based on images captured using one or more surveillance cameras installed in multiple rooms of an enterprise building, movement of the individual throughout the multiple rooms, wherein tracking movement includes controlling and reporting, via an access control system and to a metadata stream, physical access of individuals through access points within the enterprise building, a first access point of the access points permitting physical access to a room of the enterprise building and having a reader device that is included in the access control system, wherein the metadata stream includes location within the enterprise building and time stamp for the individual;

providing, based on a list of authorized computer resources, a white list identifying the individual determined, based on the metadata stream, to be in a same room as the authorized computer resources;

providing, based on a list of unauthorized computer resources, a black list identifying the individual determined, based on the metadata stream, to be in a same room as the unauthorized computer resources;

providing, based on the white list, access for the individual to the authorized computer resources within the enterprise building using an authentication server; and blocking, based on the black list, access for the individual to the unauthorized computer resources determined, based on the tracked movement of the individual within the enterprise building, to be in a same room as the individual.

6. The method as claimed in claim 5, further comprising instructing an IT system to block access to the authorized computer resources, based on the tracked movement of the individual, when individual is not present.

7. The method as claimed in claim 6, further comprising accessing an asset management database to determine locations of computer systems within the enterprise building.

8. A method, comprising:

tracking, using facial recognition to identify an individual based on images captured using one or more surveillance cameras installed in multiple rooms of an enterprise building, movement of the individual throughout the multiple rooms, wherein the tracking movement includes controlling and reporting, via an access control system, physical access of individuals through access points within the enterprise building, a first access point of the access points that permits physical access to an area of the enterprise building and having a reader device that is included in the access control system;

receiving a metadata stream of the tracked movement of the individual, wherein the metadata stream includes location within the enterprise building and time stamp for the individual;

determining, based on the metadata stream of the tracked movement of the individual, whether the individual is moving to and/or from a desk of the individual based on information from an employee resource management system including an employee database indicating location of the desk of the individual;

providing, based on a list of authorized computer resources, a white list identifying the individual determined, based on the metadata stream, to be moving to the desk of the individual associated with the authorized computer resources; and providing, based on the white list, access for the individual to the authorized computer resources.

9. The method as claimed in claim 8, further comprising determining an assigned desk location of the desk of the individual and comparing the tracked movement to the assigned desk location.

10. The method of claim 8, wherein the controlling the physical access of the individuals through the access points within the enterprise building comprises:

receiving, from a reader device installed at the first access point, one or more credentials of the individual proximate to the first access point; and causing, based on the one or more credentials, the first access point to grant physical access to the at least one of the multiple rooms.

11. The method of claim 10, where the first access point is a door, and the causing comprises sending a signal to unlock a door lock of the door.

12. A method, comprising:

tracking, by tracking systems, using facial recognition to identify an individual based on images captured using one or more surveillance cameras installed in multiple rooms of an enterprise building, movement of the individual throughout the multiple rooms, wherein the tracking systems include an access control system for controlling physical access of individuals through access points within the enterprise building, a first access point of the access points that permits physical access to a room of the enterprise building and having a reader device that is included in the access control system;

obtaining, via an employee resource management system, location of a desk of the individual, the employee resource management system including an employee database indicating the location of desks of the individuals;

receiving, by a security integration system, a metadata stream of the tracked movement of the individual, wherein the metadata stream includes location within the enterprise building and time stamp for the individual;

determining, based on the metadata stream of the tracked movement of the individual, whether the individual is moving to and/or from the desk of the individual by reference to information stored in the employee database;

providing, based on a list of authorized computer resources, a white list identifying the individual determined, based on the metadata stream, to be moving to the desk of the individual associated with the authorized computer resources; and providing, based on the white list, access for the individual to the authorized computer resources.

* * * * *